(12) United States Patent
Gho et al.

(10) Patent No.: US 11,904,259 B2
(45) Date of Patent: Feb. 20, 2024

(54) METHOD FOR ISOLATING EXTRACELLULAR VESICLES USING CATIONS

(71) Applicant: ROSETTA EXOSOME, Seoul (KR)

(72) Inventors: Yong Song Gho, Gyeongsangbuk-do (KR); Chang Jin Lee, Daegu (KR); Ji Hyun Kim, Gyeongsangbuk-do (KR); Sung Hyun Song, Gyeonggi-do (KR)

(73) Assignee: ROSETTA EXOSOME, Seoul (KR)

( * ) Notice: Subject to any disclaimer, the term of this patent is extended or adjusted under 35 U.S.C. 154(b) by 0 days.

(21) Appl. No.: 16/634,086

(22) PCT Filed: Jul. 26, 2018

(86) PCT No.: PCT/KR2018/008485
§ 371 (c)(1),
(2) Date: Jan. 24, 2020

(87) PCT Pub. No.: WO2019/022542
PCT Pub. Date: Mar. 31, 2019

(65) Prior Publication Data
US 2020/0164284 A1    May 28, 2020

(30) Foreign Application Priority Data

Jul. 26, 2017  (KR) .................. 10-2017-0094888
Jul. 26, 2018  (KR) .................. 10-2018-0087354

(51) Int. Cl.
*B01D 15/36* (2006.01)
*C12N 5/00* (2006.01)
*G01N 1/40* (2006.01)

(52) U.S. Cl.
CPC ............. *B01D 15/362* (2013.01); *C12N 5/00* (2013.01); *G01N 1/40* (2013.01)

(58) Field of Classification Search
CPC .............. B01J 20/3236; B01J 20/3265; B01D 15/3828; B01D 15/424; B01D 15/426;
(Continued)

(56) References Cited

U.S. PATENT DOCUMENTS 6,812,023 B1 * 11/2004 Lamparski ........... C12N 5/0639
                                                   435/325
6,899,863 B1 *  5/2005 Dhellin .................... B01J 41/20
                                                   424/1.21
(Continued)

FOREIGN PATENT DOCUMENTS

CN        105209881 A     12/2015
CN        106399250 A      2/2017
(Continued)

OTHER PUBLICATIONS

Wako Catalog, MagCapture Exosome Isolation Kit PS, Life Science—4 pages (Jan. 20, 2016). (Year: 2016).*
(Continued)

*Primary Examiner* — Ryan B Huang
(74) *Attorney, Agent, or Firm* — Carter, DeLuca & Farrell LLP; George Likourezos

(57) ABSTRACT

The present invention relates to a method for isolating extracellular vesicles using cations, and more particularly, to a method for isolating extracellular vesicles from various samples by using the affinity between the extracellular vesicles and cations. A method for isolating extracellular vesicles according to the present invention does not require expensive equipment, can be applied irrespective of sample amount, and has the advantage of being capable of efficiently isolating the extracellular vesicles while preserving the shape or characteristics thereof. Moreover, the method according to the present invention can be combined with existing isolation methods to maximize extracellular vesicle isolation efficiency, and can be applied to disease diagnosis,
(Continued)

disease treatment, and multi-omics research using isolated extracellular vesicles, as well as to research on the properties of extracellular vesicles.

11 Claims, 18 Drawing Sheets

(58) Field of Classification Search
CPC ........ B01D 15/3204; C12N 1/16; C12N 1/20; C12N 5/0606; C12N 5/0696; C12N 2509/00
See application file for complete search history.

(56) References Cited

U.S. PATENT DOCUMENTS

| | | | |
|---|---|---|---|
| 7,354,750 B2* | 4/2008 | Simpson | B01D 15/3828 435/174 |
| 10,465,183 B2* | 11/2019 | Skog | C12N 15/1006 |
| 10,808,240 B2* | 10/2020 | Stoll | C12N 15/11 |
| 11,730,768 B2* | 8/2023 | Badiavas | A61K 35/22 424/545 |
| 2012/0070858 A1 | 3/2012 | Contreras et al. | |
| 2014/0093880 A1* | 4/2014 | Kim | C12Q 1/6886 435/6.12 |
| 2015/0353920 A1* | 12/2015 | Enderle | C12Q 1/6806 536/25.41 |
| 2018/0120299 A1* | 5/2018 | Nishibu | C12N 15/09 |
| 2019/0040093 A1* | 2/2019 | Pendergrast | C12N 15/1006 |
| 2020/0297631 A1* | 9/2020 | Batrakova | A61K 31/337 |

FOREIGN PATENT DOCUMENTS

| | | | | |
|---|---|---|---|---|
| EP | 2889623 | A1 | 7/2015 | |
| EP | 3527980 | A1 | 8/2019 | |
| JP | 2016161480 | A | 9/2016 | |
| KR | 10-2012-0023684 | A | 3/2012 | |
| KR | 10-2016-0116802 | A | 10/2016 | |
| WO | WO-2013082518 | A1 * | 6/2013 | ............. B01D 15/20 |
| WO | 2015048566 | A1 | 4/2015 | |
| WO | 2016033695 | A1 | 3/2016 | |
| WO | WO-2016088689 | A1 * | 6/2016 | ............. C07K 17/02 |
| WO | 2016125243 | A1 | 8/2016 | |
| WO | 2017141947 | A1 | 8/2017 | |
| WO | WO-2017173034 | A1 * | 10/2017 | ......... A61K 31/4745 |

OTHER PUBLICATIONS

SAFC Biosciences, "Protein Purification Techniques, vol. 4. Metal-Chelate Affinity Chromatography," Technical Bulletin (2006), 2 pages. (Year: 2006).*
Notarangelo et al. Ultrasensitive detection of cancer biomarkers by nickel-based isolation of polydisperse extracellular vesicles from blood. EBioMedicine 43 (2019) 114-126. (Year: 2019).*
Millipore Sigma, "Immobilized Metal Chelate Affinity Chromatography (IMAC)," Extracted from Affinity Chromatography Principles and Methods, GE Healthcare, 2007, 4 pages. (Year: 2007).*
Geberc-Porekar et al. Perspectives of immobilized-metal affinity chromatography. J. Biochem. Biophys. Methods 49 (2001) 335-360. (Year: 2001).*
Santiago et al. TIM-4 structures identify a Metal Ion-dependent Ligand Binding Site where phosphatidylserine binds. Immunity. Author manuscript; available in PMC Dec. 1, 2008. p. 1-19. (Year: 2008).*
Nakai, Wataru et al. "A Novel Affinity-based Method for the Isolation of Highly Purified Extracellular Vesicles", Scientific Reports, 2016, vol. 6 33935, inner pp. 1-11 See abstract; and inner pp. 2, 3, 9.
International Search Report issued by the Korean Intellectual Property Office acting as the International Searching Authority in relation to International Application No. PCT/KR 2018/008485 dated Feb. 8, 2019.

* cited by examiner (a)

(b)

(a)

(b)

(a)

(b)

(a)

(b)

(a)

(b)

METHOD FOR ISOLATING EXTRACELLULAR VESICLES USING CATIONS

CROSS-REFERENCE TO RELATED APPLICATIONS

This application is a national phase entry under 35 U.S.C. 371 of PCT International Application No. PCT/KR2018/008485 filed Jul. 26, 2018, which claims priority to Korean Patent Application Nos. KR 10-2017-0094888, filed Jul. 26, 2017 and KR 10-2018-0087354, filed Jul. 26, 2018, the disclosure of each of these applications is expressly incorporated herein by reference in their entirety.

TECHNICAL FIELD

The present invention relates to a method for isolating extracellular vesicles using cations and, more particularly, to a method for isolating extracellular vesicles from various samples by using affinity of the extracellular vesicles to various types of cations.

BACKGROUND ART

Extracellular vesicles are nano-sized vesicles, which are naturally released by all living organisms or cells, from humans to bacteria, through universal cellular mechanisms. Extracellular vesicles derived from eukaryotic cells are involved in the differentiation of erythrocytes, regulation of immune responses, and the like, and have been especially revealed to play important roles in the progression, metastasis, or angiogenesis of cancer in cancer cell microenvironments. Therefore, extracellular vesicles have received much attention in the application as a diagnostic marker for various diseases including cancer.

Extracellular vesicles secreted from prokaryotic cells contain the constituents of prokaryotic cells similarly to the extracellular vesicles of eukaryotic cells, cause not only systemic inflammations but also an acute lung inflammation disease depending on the entrance route thereof in the human body, and has been reported to induce chronic inflammatory responses in localized skin tissues to thereby cause atopic dermatitis, as one of the representative diseases of modern people, in the skin. As a correlation between the bacteria-derived extracellular vesicles and carcinogenesis in the human body has been found, the prokaryotic cell-derived extracellular vesicles have also been receiving much attention.

One of the greatest functions of extracellular vesicles is that the extracellular vesicles serve as an important factor in an intercellular information exchange mechanism. Thus, the constituents of extracellular vesicles have also been receiving much attention in the basic and medical fields.

Extracellular vesicles, as biological nanoparticles secreted from various types of cells in vivo or in vitro, are present in body fluids, such as blood, urine, saliva, and tears, include a lipid bilayer derived from cells, and are membrane-structured vesicles having various sizes in a range of 20-10,000 nm.

Extracellular vesicles bind to other cells and tissues to act as a transporter vehicle, which carry intracellular substances, such as membrane components, proteins, and RNA, and thus contain proteins, lipids, amino acids, RNA, and the like of original cells (mother cells), from which the extracellular vesicles are secreted. Therefore, extracellular vesicles are an important basis for understanding physiological and pathological characteristics of mother cells. Additionally, it has been known that nucleic acids, growth hormones, proteins, and the like contained in the extracellular vesicles are protected by cellular membrane-type phospholipids and thus can perform more stable functions than soluble forms of growth factors and cytokines, and as a result, the importance of extracellular vesicles is increasingly growing, and the substances contained in the extracellular vesicles are expected to have, after being analyzed, utilization for various uses, including diagnosis and treatment of diseases.

Extracellular vesicles are small with a size in the nanometer level, and numerous substances in addition to the extracellular vesicles are present in body fluids, cell cultures, and the like. Therefore, the isolation of extracellular vesicles from samples, such as body fluids and cell cultures, is important for analysis of the extracellular vesicles, and corresponds to one of the most core techniques in all the fields in which extracellular vesicles are utilized.

In recent years, the utilization of a non-invasive liquid biopsy in the diagnosis of diseases has been developed from various angles. In addition, efforts have been made to discover novel markers for disease diagnosis by utilizing extracellular vesicles in living tissues or body fluids and to perform a diagnosis by using the markers. The underlying problem with these efforts lies in the isolation of extracellular vesicles from living tissues or body fluids, and the conventional purification of extracellular vesicles from body fluids showing relatively limited amounts and high complexity is almost impossible. Hence, there is an urgent need for a novel efficient isolation method, which is distinguished from conventional methods for isolating extracellular vesicles.

An existing technique used in the isolation of extracellular vesicles is ultracentrifugation, size exclusion, immunoaffinity isolation, microfluidics chip, or precipitation using polymers, and out of these, ultracentrifugation is most widely used. However, the isolation of extracellular vesicles through ultracentrifugation shows limitations, such as consuming a lot of labor and time due to complicated steps, requiring expensive equipment, and having a low yield, and thus such an isolation is very limited in the application to a purification for medicinal products, which requires a large amount of extracellular vesicles, as well as a clinical diagnosis, which requires rapid results by using only a small amount of a sample.

One of the most efficient methods in the isolation of substances is that contaminants are sequentially removed from an environment having complexity by using the selective binding to a target substance while the target substance is not lost during an isolation of the target substance. However, as for extracellular vesicles, examples of a material having such a selective binding property are limited to some antibodies or protein ligands. The isolation of extracellular vesicles using these antibodies or proteins is inefficient, makes it difficult to develop antibodies and protein ligands at high efficiency, and requires high cost, and thus is very limited.

Therefore, there is an urgent need for a technique for efficiently and selectively isolating and purifying extracellular vesicles with a high yield while maintaining the structures and functions of extracellular vesicles intact.

DETAILED DESCRIPTION OF THE INVENTION

Technical Problem

An aspect of the present invention is to provide a method for isolating extracellular vesicles in a sample conveniently and highly efficiently by using the affinity between cations and extracellular vesicles, which has not been reported so far.

Technical Solution

The present invention has been made to solve the above-mentioned problems, and an aspect of the present invention is to provide a method for isolating extracellular vesicles in a sample conveniently and highly efficiently by using the affinity between cations and extracellular vesicles.

In the present invention, when various types of cations are added to react with various samples containing extracellular vesicles, the extracellular vesicles and the cations bind to each other to form insoluble complexes in the samples. The extracellular vesicle-cation complexes can be separated by a variety of methods, such as centrifugation, ultrafiltration, and precipitation by gravity, and subsequently, the extracellular vesicles can be isolated by desorption of the cations from the complexes. Through such a procedure, the extracellular vesicles can be isolated from various samples promptly and easily without physicochemical transformations, and the extracellular vesicles thus isolated are easy to utilize in diagnosis, treatment, multi-omics study, study of characteristics of extracellular vesicles, and the like.

The term used herein, "extracellular vesicles" collectively refers to biological nanoparticles derived from cells of Archaea, Prokarya, or Eukarya, and may include exosomes, argosomes, dexosomes, ectosomes, exovesicles, oncosomes, prominosomes, prostasomes, tolerosomes, microparticles, microvesicles, nanovesicles, blebbing vesicles, budding vesicles, exosome-like vesicles, matrix vesicles, membrane vesicles, shedding vesicles, membrane particles, shedding microvesicles, membrane blebs, epididimosomes, promininosomes, texosomes, and archeosomes, but are not limited thereto.

In accordance with an aspect of the present invention, there is provided a method for isolating extracellular vesicles, the method including: (a) adding cations to a biological sample; (b) reacting the cations with extracellular vesicles contained in the biological sample to form an extracellular vesicle-cation complex; (c) separating the extracellular vesicle-cation complex from the sample; and (d) separating the cations from the complex to purify extracellular vesicles.

A method for isolating extracellular vesicles according to an embodiment of the present invention is schematically shown in FIG. 1.

In an embodiment of the present invention, a method for isolating extracellular vesicles includes: a step of adding cations to a biological sample (step (a)); and a step of reacting the cations with extracellular vesicles contained in the biological sample to form an extracellular vesicle-cation complex (step (b)).

The term used herein "biological sample" or "sample" includes a biosample, a cell culture, a tissue sample, and the like, each of which contains extracellular vesicles. Specifically, the sample may be at least one selected from the group consisting of mammalian cell culture medium, bacterial cell culture medium, yeast culture medium, a tissue extract, a cancer tissue, serum, blood plasma, saliva, tears, sweat, urine, feces, cerebrospinal fluid (CSF), ascites, amniotic fluid, semen, milk, dust, fresh water, seawater, soil, and a fermented food, but is not limited thereto.

The term used herein, "cation" refers to a positively charged ion, which has specific affinity to extracellular vesicles and can bind to extracellular vesicles in a sample, and the cation may be preferably a metal cation. The term used herein, "metal cation" may include an alkali metal ion, an alkaline earth metal ion, a transition metal ion, and a post-transition metal ion. The cation or metal cation of the present invention may be preferably a transition metal ion or an alkaline earth ion, but is not delimited thereto as long as the cation has specific affinity to extracellular vesicles to be isolated.

Alkali metal is a general term for all chemical elements, excluding hydrogen, in group 1 of the periodic table, and includes lithium (Li), sodium (Na), potassium (K), rubidium (Rb), cesium (Cs), and francium (Fr). Alkaline earth metal is an element of group 2 in the periodic table, and includes beryllium (Be), magnesium (Mg), calcium (Ca), strontium (Sr), barium (Ba), and radium (Ra). The transition metal includes elements of periods 4-7 and groups 3-12 in the periodic table, and is present in the form of a complex ion by forming an ionic bond compound together with a nonmetal. Specifically, the transition metal of the present invention includes scandium (Sc), yttrium (Y), titanium (Ti), zirconium (Zr), hafnium (Hf), rutherfordium (Rf), vanadium (V), niobium (Nb), tantalum (Ta), dubnium (Db), chromium (Cr), molybdenum (Mo), tungsten (W), seaborgium (Sg), manganese (Mn), technetium (Tc), rhenium (Re), bohrium (Bh), iron (Fe), ruthenium (Ru), osmium (Os), hassium (Hs), cobalt (Co), rhodium (Rh), iridium (Ir), meitnerium (Mt), nickel (Ni), palladium (Pd), platinum (Pt), darmstadtium (Ds), copper (Cu), silver (Ag), gold (Au), roentgenium (Rg), zinc (Zn), cadmium (Cd), mercury (Hg), and copernicium (Cn). A post-transition metal means a metal element of the p-block in the periodic table, and includes aluminum (Al), gallium (Ga), indium (In), thallium (Tl), tin (Sn), lead (Pb), bismuth (Bi), and polonium (Po).

The addition of cations of the present invention includes an addition of a solution containing cations to a sample and an addition of cations in a solid form to a sample and dissolving the cations; but the addition of cations is not limited thereto as long as a cationic form can react with extracellular vesicles in a sample.

The method for isolating extracellular vesicles of the present invention is directed to a method of isolating extracellular vesicles binding to cations from a sample by using the property of the extracellular vesicles to be isolated to specifically binding to cations. In the method of the present invention, the cations are first added to react with the sample to induce a specific binding between the extracellular vesicles in the sample and the cations, thereby forming an insoluble type extracellular vesicle-cation complex.

An example of the present invention verified that calcium ions, manganese ions, cobalt ions, copper ions, or zinc ions were added to a culture medium sample or a urine sample containing extracellular vesicles to form an insoluble complex. It was also verified that the insoluble complex was settled by gravity and thus could be easily separated.

In an embodiment of the present invention, the method for isolating extracellular vesicles of the present invention includes a step of separating the extracellular vesicle-cation complex from the sample (step (c)).

The step of separating the extracellular vesicle-cation complex is that the insoluble complex formed in the previous step is separated from the sample containing a variety of soluble materials. The step may adopt at least one selected from centrifugation, ultracentrifugation, filtration, ultrafiltration, gravity, sonication, density-gradient ultracentrifugation, size-exclusion chromatography, ion-exchange chromatography, affinity chromatography, polymer-based precipitation, or organic solvent precipitation, but is not limited thereto.

In an embodiment of the present invention, the method for isolating extracellular vesicles of the present invention includes a step of separating the cations from the extracellular vesicle-cation complex to purify extracellular vesicles (step (d)).

The step of purifying extracellular vesicles in the present invention is that only the extracellular vesicles can be separated from the complex by removing the specific binding state between the extracellular vesicles and the cations, and the step can employ various methods or conditions that could be understood by a person skilled in the art.

In an embodiment of the present invention, the step may include adding a chelating agent to the separated extracellular vesicle-cation complex.

The term used herein, "chelating agent" or "chelating ligand" refers to an ion, a molecule, or an atomic group containing two or more coordinating atoms, which is coordinated to a metal ion to form a stable chelate complex. The term is also called a tridentate ligand, a tetradentate ligand, a pentadentate ligand, a hexadentate ligand, or the like, according to the number of coordinating atoms. The chelating ligand of the present invention may be at least one selected from the group consisting of iminodiacetic acid (IDA), nitrilotriacetic acid (NTA), tris-(carboxymethyl)ethylenediamine (TED), ethylenediamine, ethylendiamine tetraacetate (EDTA), alkylene diamine triacetic acid, diethylenetriaminepentaacetic acid (DTPA), ethylene glycol-bis(β-aminoethyl ether)-N,N,N',N'-tetraacetic acid (EGTA), phosphoserine, and 1,4,7-triazocyclononane (TACN), but is not limited thereto as long as the chelating ligand can specifically bind to metal cations used in the present invention to separate the cations from the extracellular vesicle-cation complex.

In an embodiment of the present invention, the step may employ changing the pH value of a solution containing the separated extracellular vesicle-cation complex.

In an embodiment of the present invention, the step may employ purifying the extracellular vesicles from the complex by changing the concentration of imidazole, histidine, ethylendiamine tetraacetate (EDTA), or a salt in the solution containing the separated extracellular vesicle-cation complex.

The step of purifying extracellular vesicles in the present invention may be performed by selecting any one of the above methods or one or more thereof in combination. Preferably, the purification condition of the present invention may employ a buffer of pH 10 or lower, 0-5 M NaCl, 0-2 M imidazole, a 0-2 M metal chelating agent, or a combination thereof, but is not limited thereto.

In an embodiment of the present invention, the method for isolating extracellular vesicles of the present invention may further include a step of pre-treating the sample before the cations are added to the sample.

The pre-treatment step of the present invention is a step of partially purifying a non-purified sample, and may adopt at least one selected from centrifugation, ultracentrifugation, filtration, ultrafiltration, sonication, density gradient ultracentrifugation, size-exclusion chromatography, ion-exchange chromatography, affinity chromatography, polymer-based precipitation, or organic solvent precipitation, but is not limited thereto.

In an embodiment of the present invention, the method for isolating extracellular vesicles of the present invention may further include a step of post-treating the separated extracellular vesicles.

The post-treatment step of the present invention is a step of purifying the separated extracellular vesicles, and may adopt at least one selected from centrifugation, ultracentrifugation, filtration, ultrafiltration, sonication, density gradient ultracentrifugation, size-exclusion chromatography, ion-exchange chromatography, affinity chromatography, polymer-based precipitation, or organic solvent precipitation, but is not limited thereto.

In an embodiment of the present invention, the method for isolating extracellular vesicles of the present invention may further include a step of adding a polymer or salting-out ions in the step of adding cations to the sample. In the method for isolating extracellular vesicles using cations in the present invention, the addition of the polymer or salting-out ions together with the cations can significantly increase the formation rate of the insoluble complex and remarkably improve the isolation efficiency of extracellular vesicles and the isolation time thereof.

Specifically, the polymer or salting-out ions may be added to the sample simultaneously with the cations.

In addition, the polymer or salting-out ions may be added to the sample in advance before the addition of cations to the sample.

In addition, the polymer or salting-out ions may be added to the sample after the addition of the cations.

In an embodiment of the present invention, the polymer may be polyethylene glycol (PEG) or polyoxazoline, wherein the polyoxazoline may be poly(2-methyl-2-oxazoline) (PMOZ), poly(2-ethyl-2-oxazoline) (PEOZ), or poly(2-propyl-2-oxazoline) (PPOZ) depending on the substituent thereof. The polymer may be preferably polyethylene glycol (PEG) or poly(2-ethyl-2-oxazoline) (PEOZ), but is not limited thereto.

The term used herein, "salting-out ion" refers to a kosmotropic salt that stabilizes the structure of water, wherein the salting-out ion is used to increase the intensity of a hydrophobic interaction by reducing the solubility of water in a solution. Kosmotropic salts are expressed by the Hofmeister series according to the ability to influence the solubility of a soluble material in a solution, and the anionic series are as follows: $^-SO_4^{2-} > HPO_4^{2-} > OH^- > F^- > HCOO^- > CH_3COO^- > Cl^- > Br^- > NO_3^- > I^- > SCN^- > ClO_4^-$.
The cationic series are as follows: $NH_4^+ < Rb^+ < K^+ < Na^+ < Cs^+ < Li^+ < Ca^{2+} < Mg^{2+} < Ba^{2+}$. Kosmotropic salts act as salting-out ions for hydrophobic particles according to the Hofmeister series. The salting-out ions of the present invention may be a kosmotropic salt composed of an anion of Hofmeister series that stabilizes the structure of water and the counter cation thereof.

Advantageous Effects

The method for isolating extracellular vesicles according to the present invention does not require expensive equipment, such as a centrifuge, and prevents the exposure of a sample to extreme environments during the isolation of extracellular vesicles, and thus can efficiently isolate extracellular vesicles while maintaining the morphology or properties of the extracellular vesicles. Furthermore, the method of the present invention can be applied in conjunction with a conventional method for isolating extracellular vesicles, wherein the method of the present invention can be applied before or after the conventional method is performed, thereby maximizing the efficiency of isolation.

Furthermore, the method for isolating extracellular vesicles of the present invention enables the simple and effective isolation of extracellular vesicles and thus can be utilized as an important factor in the mass-purification of extracellular vesicles, and enables the application in pre-treatment and post-treatment steps of a small amount of a body fluid sample and thus can be also utilized in clinical diagnosis.

Furthermore, the method for isolating extracellular vesicles of the present invention can fractionate subsets of extracellular vesicles through various types of cations by using the feature that the affinity to a particular type of cations varies depends on the type of extracellular vesicles. The fractionated subsets of extracellular vesicles can be utilized for multi-dimensional disease diagnosis, and the application of a variety of previously developed disease diagnostic markers to the present invention can solve problems of conventional diagnostic markers and make various applications of the diagnostic markers.

MODE FOR CARRYING OUT THE INVENTION

Hereinafter, the present invention will be described in more detail with reference to examples. These examples are intended to only illustrate the present invention, and it would be obvious to those skilled in the art that the scope of the present invention is not construed as being limited to the examples.

Example 1

Purification and Analysis of Sample Extracellular Vesicles

A colorectal cancer cell SW480 culture was centrifuged at 500×g for 10 min (repeated twice in total) to remove remaining cells and precipitates. The supernatant was again centrifuged at 2,000×g for 20 min (repeated twice in total) to remove precipitates.

To primarily purify and precipitate extracellular vesicles present in the supernatant, the supernatant was subjected to addition of an extracellular vesicle precipitation-inducing solution (8.4% polyethylene glycol 6000, 250 mM NaCl, 20 mM HEPES, pH 7.4), stored in a refrigerator for 16 hrs, and centrifuged at 12,000×g for 30 min to harvest the precipitated extracellular vesicles, which were then dissolved in HEPES-buffered saline (20 mM HEPES, 150 mM NaCl, pH 7.4).

To secondarily purify extracellular vesicles using density and buoyancy, the sample was mixed with Optiprep (to a final concentration of 30%), and placed at the lowest layer in an ultracentrifugation container, and then 20% OptiPrep and 5% OptiPrep were layered thereon in that order. After OptiPrep buoyant density gradient ultracentrifugation (30%, 20%, and 5% OptiPrep triple layers) at 200,000×g for 2 hrs was performed, a zone having an equivalent density (1.08-1.12 g/ml) to extracellular vesicles after the ultracentrifugation was harvested.

To tertiarily purify the purified extracellular vesicles, the purified extracellular vesicles were loaded onto a column (10×100 mm) charged with Sephacryl S500 by using HPLC equipment, followed by size-exclusion chromatography, thereby harvesting the finally purified extracellular vesicle fractions. The present procedure for isolating sample extracellular vesicles is shown in FIG. 2A.

Figure 1:
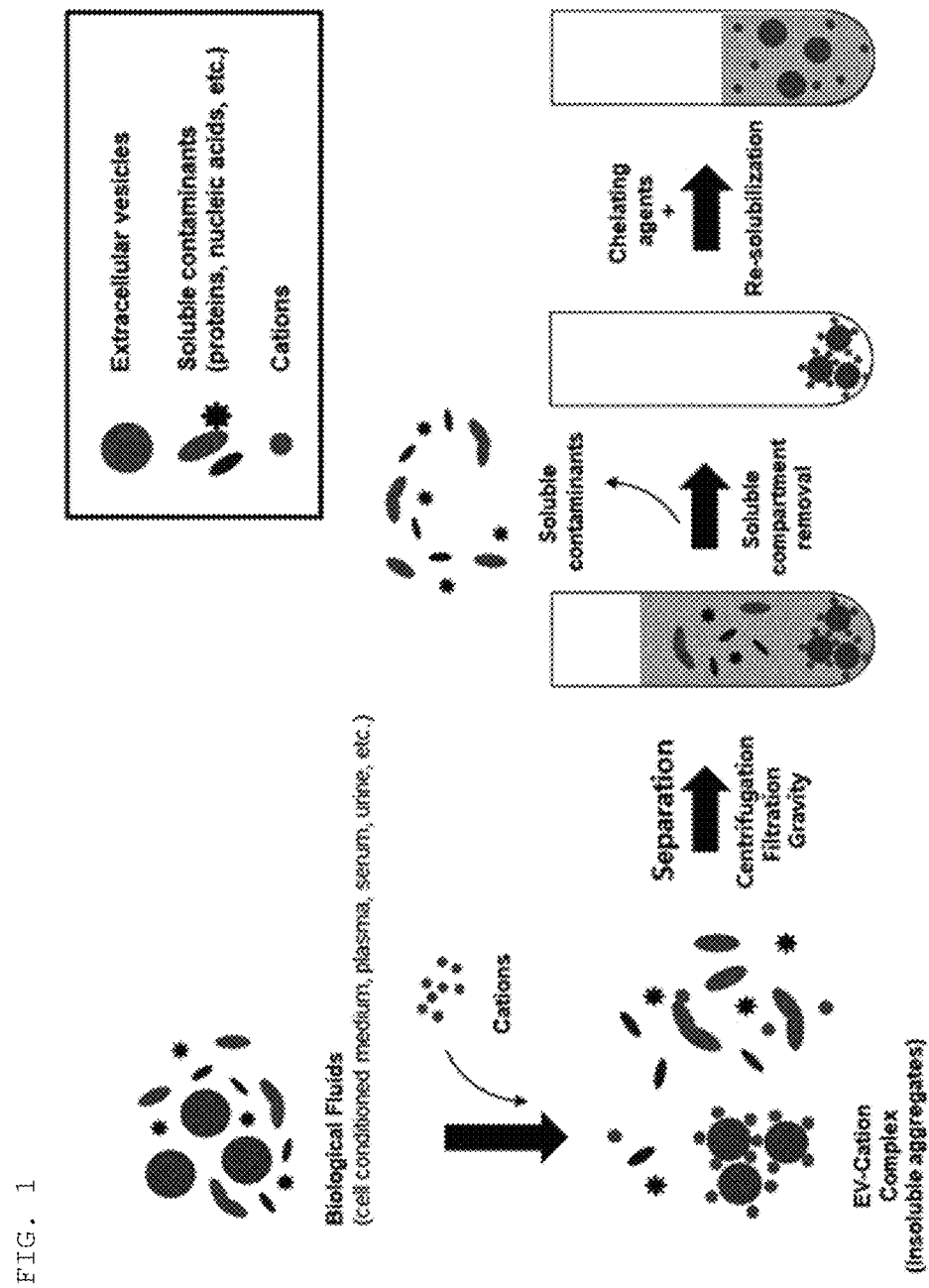
FIG. 1 is a schematic view showing a method for isolating extracellular vesicles according to an embodiment of the present invention.
Figure 2:
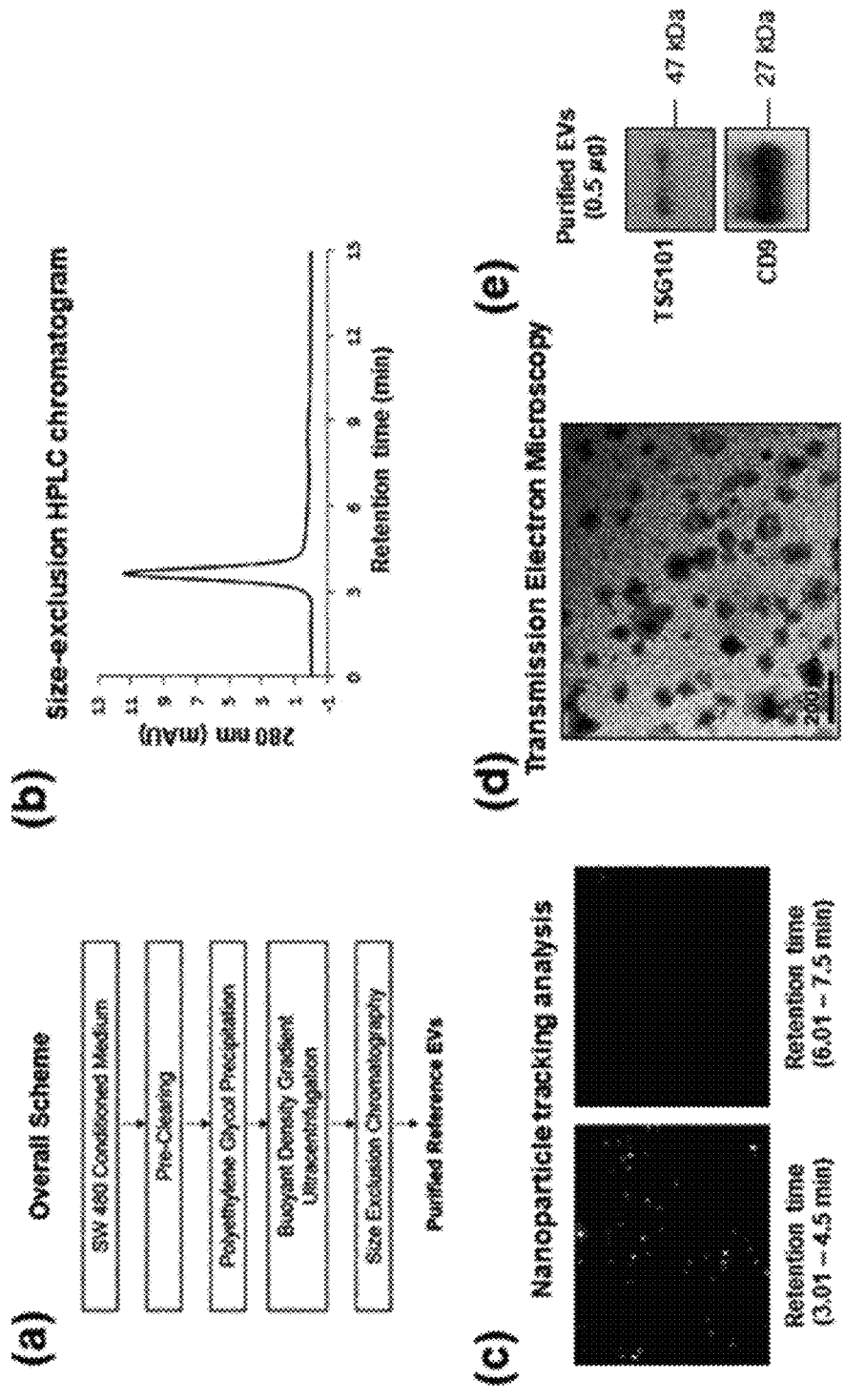
FIGS. 2a, 2b, 2c, 2d and 2e show a method for isolating sample extracellular vesicles and characteristic analysis results thereof according to an example of the present invention.

As a result of analyzing the purified colorectal cancer cell-derived extracellular vesicles through the HPLC chromatogram, the 280-nm absorbance band was observed at 3.6 min in the molecular-size exclusion chromatography (FIG. 2B). As a result of nanoparticle tracking analysis (NTA) of the respective fractions through chromatography, high nanoparticle signals could be detected in samples eluted between 3.01-4.5 min, and these signals were verified to match the 280-nm absorbance band, which indicates that extracellular vesicles correspond to the band detected at 3.6 min in the HPLC analysis (FIG. 2B).

The extracellular vesicles finally purified from the colorectal cancer cell lines (SW480) by the above method were checked for morphology. As shown in FIG. 2D, the results verified that the colorectal cancer cell SW480-derived extracellular vesicles were about 50-200 nm in size. The extracellular vesicle markers TSG101 and CD9 were confirmed through western blotting, and are shown in FIG. 2E.

Example 2

Isolation of Extracellular Vesicles Using Various Types of Cations with Several Concentrations Colorectal cancer cell cultures were subjected to addition of various types of cations ($Ca^{2+}$, $Cu^{2+}$, $Zn^{2+}$) with several concentrations, followed by mixing and then centrifugation at 3,000×g for 10 min, to thereby harvest precipitates, which were then dissolved in HEPES-buffered saline containing 50 mM EDTA. As a result of analysis of the isolated extracellular vesicles by size-exclusion chromatography using an HPLC system, the sample extracellular vesicles were detected at 3.6 min and are shown in FIG. 3A.

Figure 3:
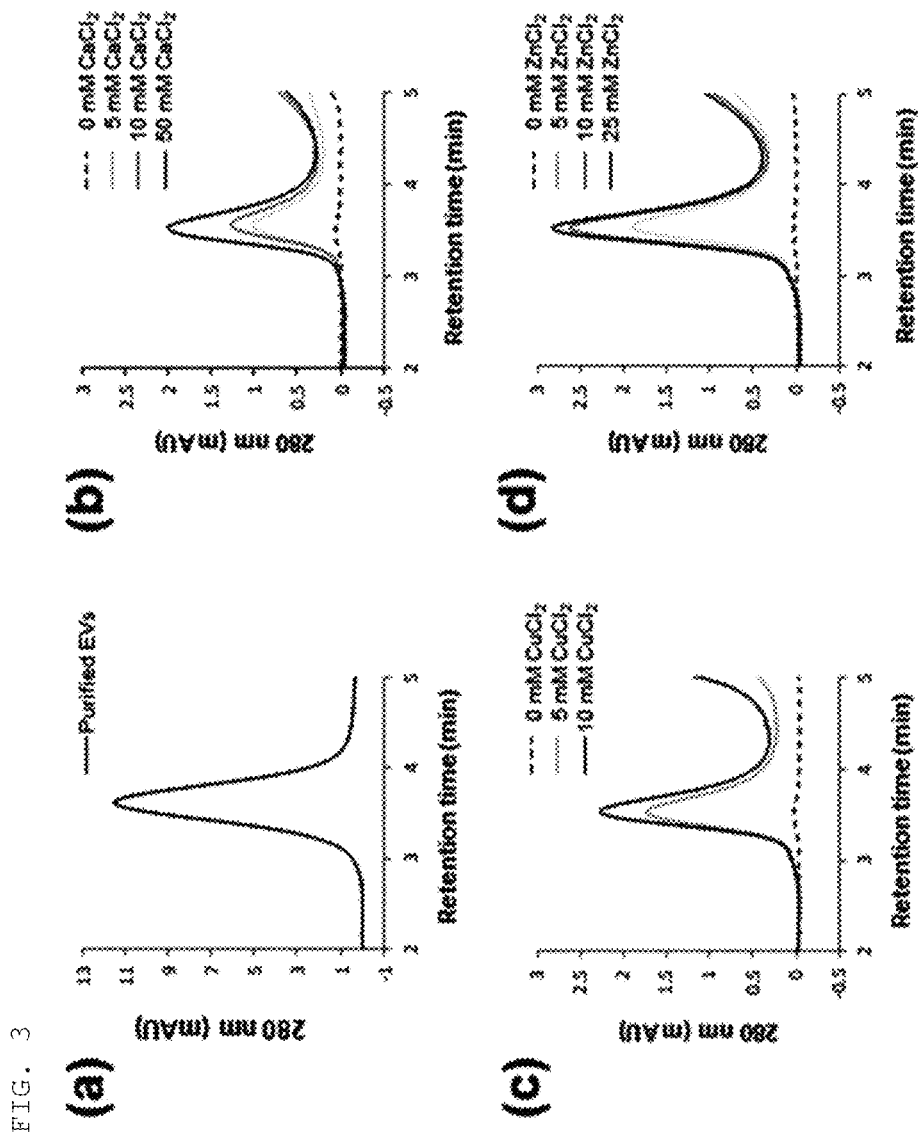
FIGS. 3a, 3b, 3c and 3d show HPLC results confirming that extracellular vesicles were isolated from cell cultures by the addition of various types of cations ($Ca^{2+}$, $Cu^{2+}$, and $Zn^{2+}$) with several concentrations according to an example of the present invention.

As for the treatment concentrations of calcium, copper, and zinc cations added to the colorectal cancer cell cultures, it was verified that the 280-nm absorbance band detected at 3.6 min increased in proportion with the concentration of cations, and these results are shown in FIGS. 3B to 3D. The absorbance bands in the respective types of cations and the absorbance band in the sample extracellular vesicles showed the same detection time, and it could be seen that the yield of extracellular vesicles isolated from the cell cultures increases according to the concentration of cations added.

Example 3

Isolation of Extracellular Vesicles Using Copper Cations (Copper(II) Chloride)

Colorectal cancer cell cultures were subjected to addition of copper cations with several concentrations, followed by mixing and then centrifugation at 3,000×g for 10 min, to thereby harvest precipitates, which were then dissolved in HEPES-buffered saline containing 50 mM EDTA. The extracellular vesicles isolated by the above method were investigated by nanoparticle tracking analysis and western blot analysis. For nanoparticle tracking analysis, the Nanosight LM10 instrument was used, and tracking and recording was made under the conditions of a camera level of 10 and a detection limit of 3 for 60 sec. For western blot analysis, the signal of CD9, which is a general extracellular vesicle marker, was analyzed after SDS electrophoresis.

Figure 4:
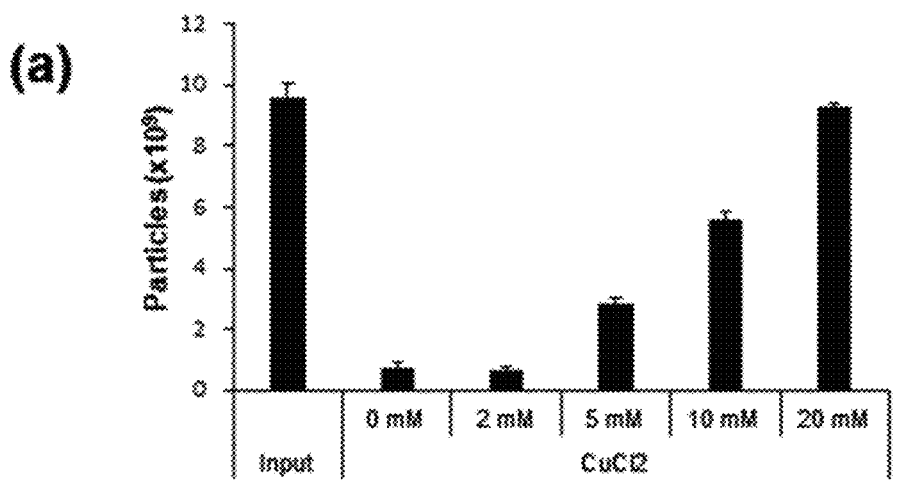
FIG. 4 shows nanoparticle tracking analysis results (FIG. 4A) and western blotting results (FIG. 4B) confirming that extracellular vesicles were isolated from cell cultures by addition of copper cations (copper(II) chloride) with several concentrations according to an example of the present invention.
Figure 4:
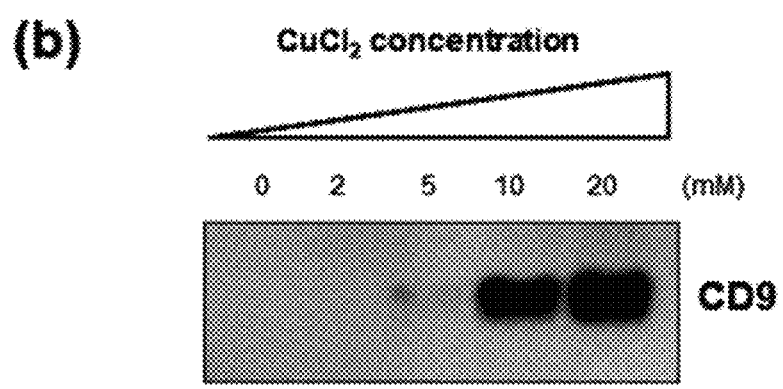

As a result, it was shown in FIG. 4A that the yield of extracellular vesicles increased as the concentration of copper cations increased, and it was therefore confirmed in FIG. 4B that the signal of the general extracellular vesicle marker CD9 increased in proportion with the concentration of copper cations.

Example 4

Isolation of Extracellular Vesicles Using Copper Cations (Copper(II) Sulfate)

Colorectal cancer cell cultures were subjected to addition of copper cations with several concentrations, followed by mixing and then centrifugation at 3,000×g for 10 min, to thereby harvest precipitates, which were then dissolved in HEPES-buffered saline containing 50 mM EDTA. The extracellular vesicles isolated by the above method were investigated by nanoparticle tracking analysis and western blot analysis.

Figure 5:
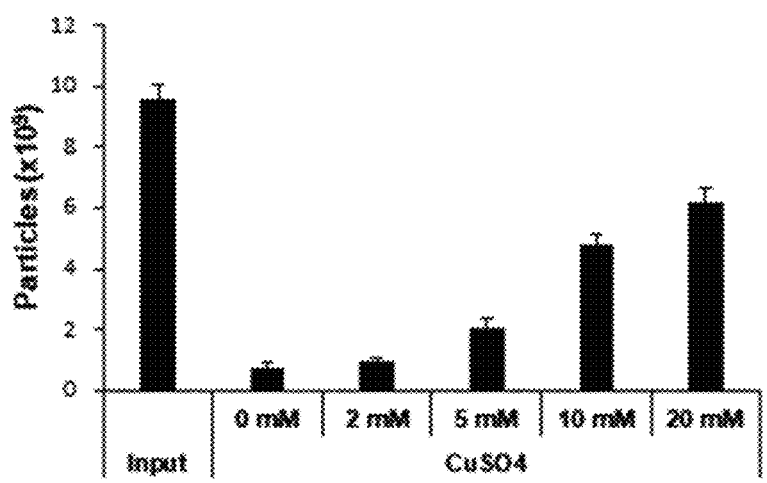
FIG. 5 shows nanoparticle tracking analysis results (FIG. 5A) and western blotting results (FIG. 5B) confirming that extracellular vesicles were isolated from cell cultures by addition of copper cations (copper(II) sulfate) with various concentrations according to an example of the present invention.
Figure 5:
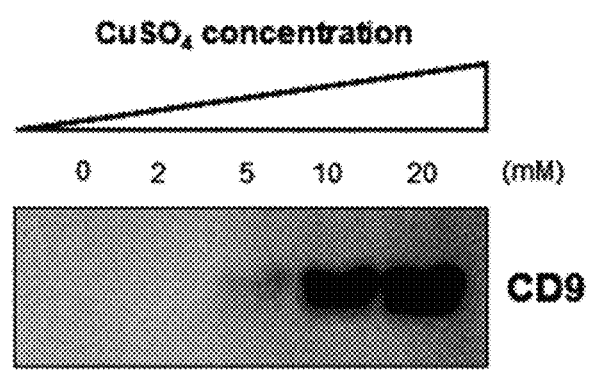

As a result, it was shown in FIG. 5A that the concentration of extracellular vesicles increased as the concentration of copper cations increased, and it was therefore confirmed in FIG. 5B that the signal of the general extracellular vesicle marker CD9 increased in proportion with the concentration of copper cations.

Example 5

Isolation of Extracellular Vesicles Using Cobalt Cations (Cobalt Chloride)

Colorectal cancer cell cultures were subjected to addition of cobalt cations with several concentrations, followed by mixing and then centrifugation at 3,000×g for 10 min, to thereby harvest precipitates, which were then dissolved in HEPES-buffered saline containing 50 mM EDTA. The extracellular vesicles isolated by the above method were investigated by nanoparticle tracking analysis and western blot analysis.

Figure 6:
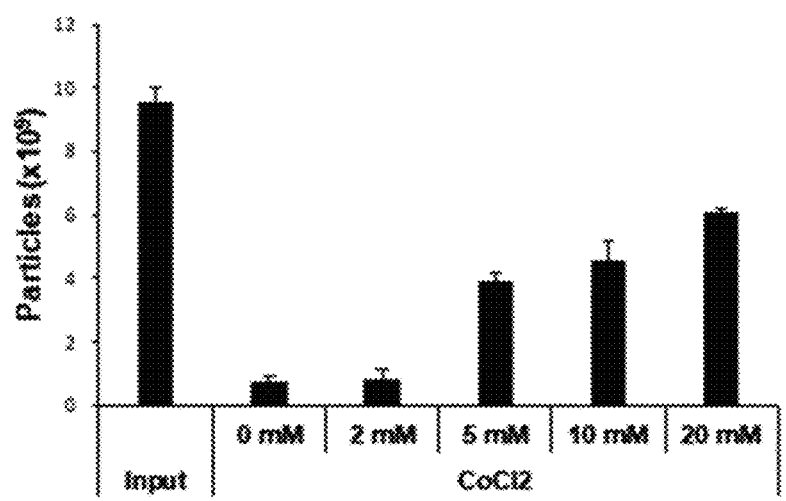
FIG. 6 shows nanoparticle tracking analysis results (FIG. 6A) and western blotting results (FIG. 6B) confirming that extracellular vesicles were isolated from cell cultures by addition of cobalt cations (cobalt chloride) with various concentrations according to an example of the present invention.
Figure 6:
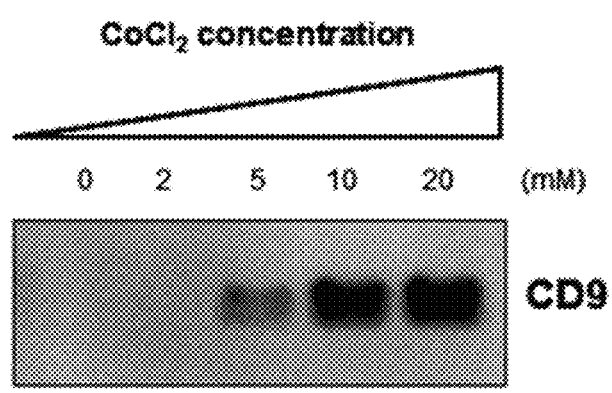

As a result, it was shown in FIG. 6A that the concentration of extracellular vesicles increased as the concentration of cobalt cations increased, and it was therefore confirmed in FIG. 6B that the signal of the general extracellular vesicle marker CD9 increased in proportion with the concentration of cobalt cations.

Example 6

Isolation of Extracellular Vesicles Using Manganese Cations (Manganese(II) Chloride)

Colorectal cancer cell cultures were subjected to addition of manganese cations with several concentrations, followed by mixing and then centrifugation at 3,000×g for 10 min, to thereby harvest precipitates, which were then dissolved in HEPES-buffered saline containing 50 mM EDTA. The extracellular vesicles isolated by the above method were investigated by nanoparticle tracking analysis and western blot analysis.

Figure 7:
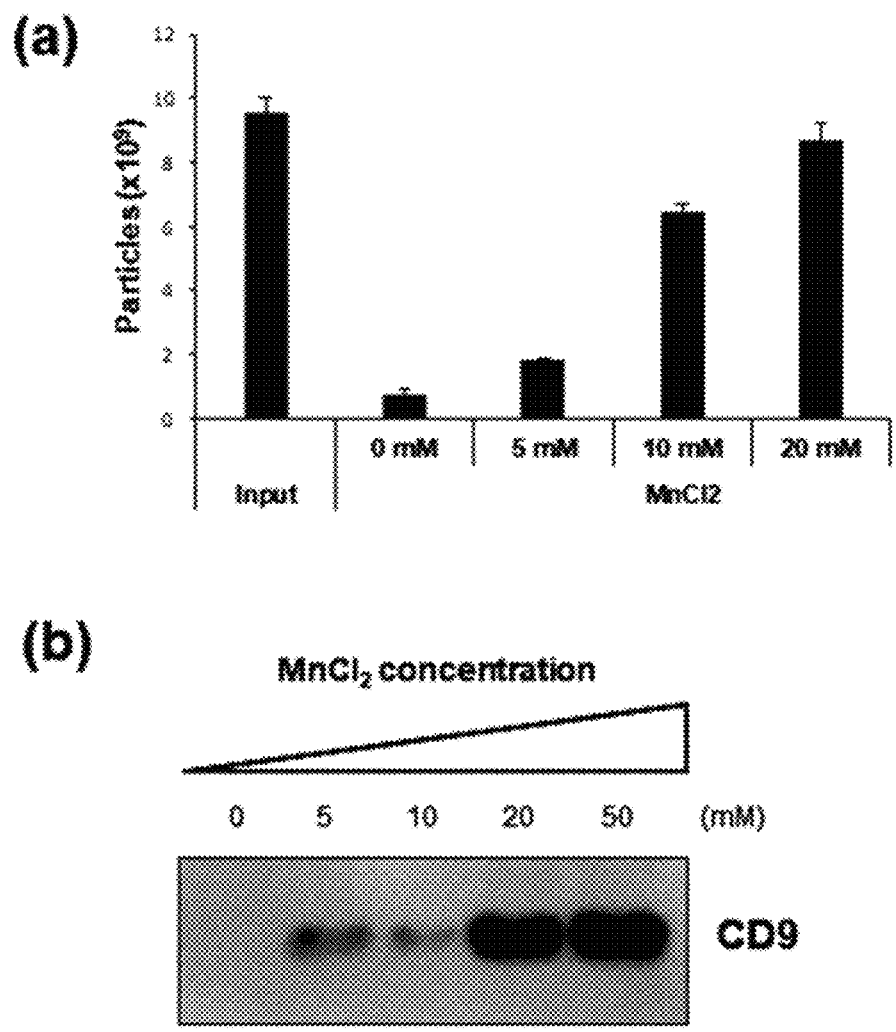
FIG. 7 shows nanoparticle tracking analysis results (FIG. 7A) and western blotting results (FIG. 7B) confirming that extracellular vesicles were isolated from cell cultures by addition of manganese cations (manganese(II) chloride) with various concentrations according to an example of the present invention.

As a result, it was shown in FIG. 7A that the concentration of extracellular vesicles increased as the concentration of manganese cations increased, and it was therefore confirmed in FIG. 7B that the signal of the general extracellular vesicle marker CD9 increased in proportion with the concentration of manganese cations.

Example 7

Isolation of Extracellular Vesicles Using Manganese Cations (Manganese(II) Sulfate)

Colorectal cancer cell cultures were subjected to addition of manganese cations with several concentrations, followed by mixing and then centrifugation at 3,000×g for 10 min, to thereby harvest precipitates, which were then dissolved in HEPES-buffered saline containing 50 mM EDTA. The extracellular vesicles isolated by the above method were investigated by nanoparticle tracking analysis and western blot analysis.

Figure 8:
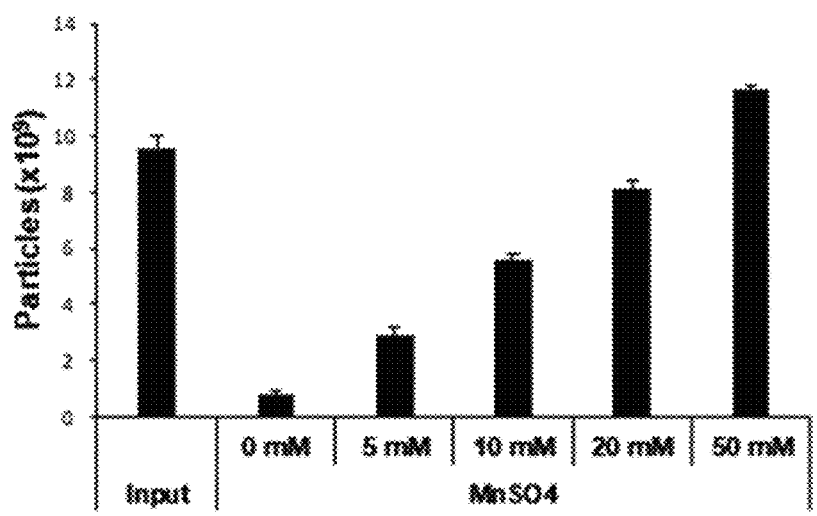
FIG. 8 shows nanoparticle tracking analysis results (FIG. 8A) and western blotting results (FIG. 8B) confirming that extracellular vesicles were isolated from cell cultures by addition of manganese cations (manganese(II) sulfate) with various concentrations according to an example of the present invention.
Figure 8:
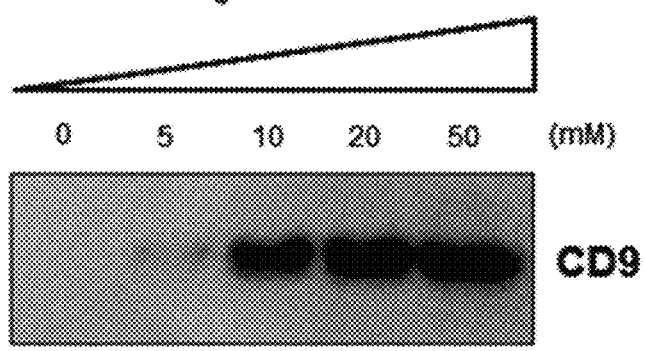

As a result, it was shown in FIG. 8A that the concentration of extracellular vesicles increased as the concentration of manganese cations increased, and it was therefore confirmed in FIG. 8B that the signal of the general extracellular vesicle marker CD9 increased in proportion with the concentration of manganese cations.

Example 8

Isolation of Extracellular Vesicles Using Calcium Cations (Calcium Chloride)

Colorectal cancer cell cultures were subjected to addition of calcium cations with several concentrations, followed by mixing and then centrifugation at 3,000×g for 10 min, to thereby harvest precipitates, which were then dissolved in HEPES-buffered saline containing 50 mM EDTA. The extracellular vesicles isolated by the above method were investigated by nanoparticle tracking analysis and western blot analysis.

Figure 9:
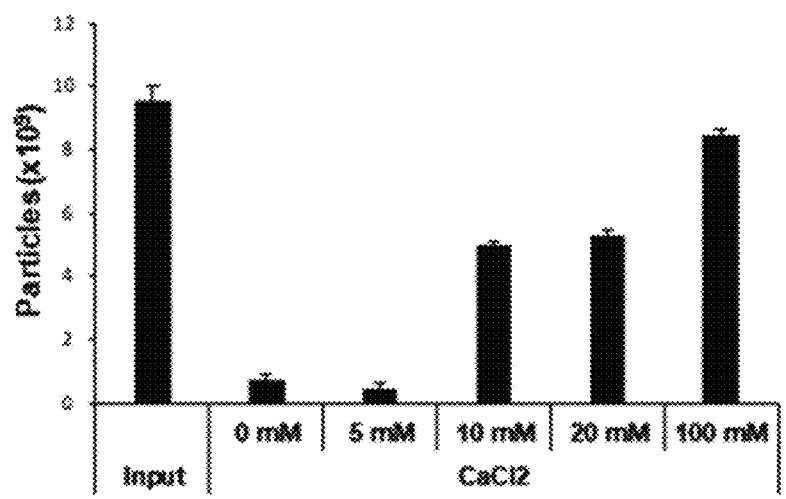
FIG. 9 shows nanoparticle tracking analysis results (FIG. 9A) and western blotting results (FIG. 9B) confirming that extracellular vesicles were isolated from cell cultures by addition of calcium cations (calcium chloride) with various concentrations according to an example of the present invention.
Figure 9:
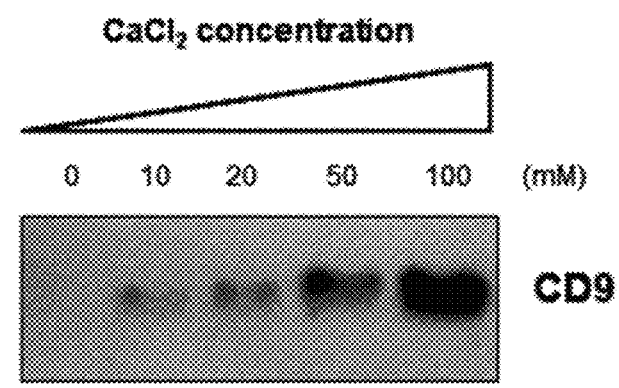

As a result, it was shown in FIG. 9A that the concentration of extracellular vesicles increased as the concentration of calcium cations increased, and it was therefore confirmed in FIG. 9B that the signal of the general extracellular vesicle marker CD9 increased in proportion with the concentration of calcium cations.

Example 9

Isolation of Extracellular Vesicles Using Zinc Cations (Zinc Chloride)

Colorectal cancer cell cultures were subjected to addition of zinc cations with several concentrations, followed by mixing and then centrifugation at 3,000×g for 10 min, to thereby harvest precipitates, which were then dissolved in HEPES-buffered saline containing 50 mM EDTA. The extracellular vesicles isolated by the above method were investigated by nanoparticle tracking analysis and western blot analysis.

Figure 10:
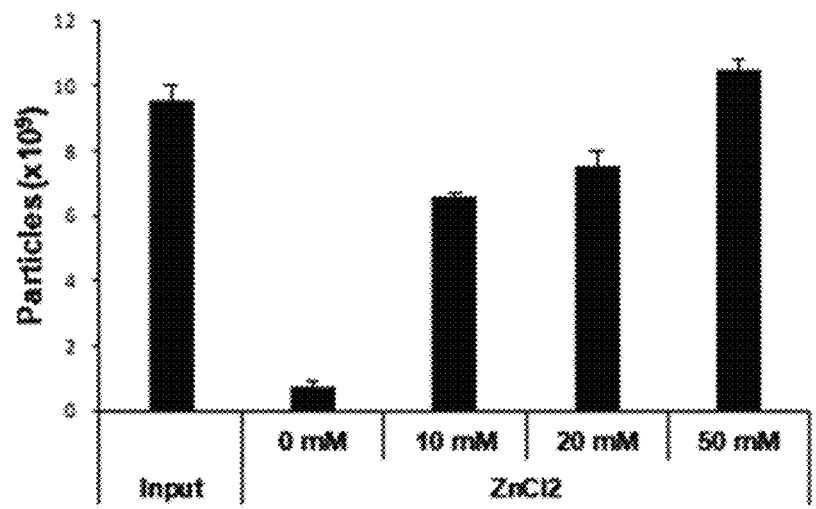
FIG. 10 shows nanoparticle tracking analysis results (FIG. 10A) and western blotting results (FIG. 10B) confirming that extracellular vesicles were isolated from cell cultures by addition of zinc cations (zinc chloride) with various concentrations according to an example of the present invention.
Figure 10:
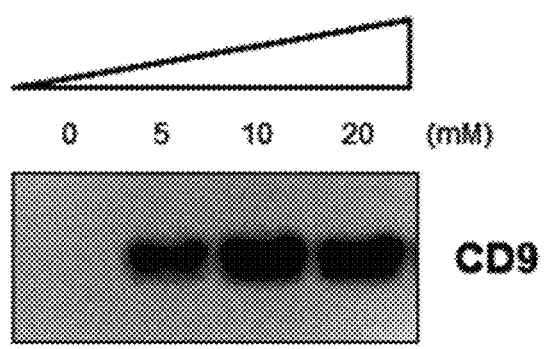

As a result, it was shown in FIG. 10A that the concentration of extracellular vesicles increased as the concentration of zinc cations increased, and it was therefore confirmed in FIG. 10B that the signal of the general extracellular vesicle marker CD9 increased in proportion with the concentration of zinc cations.

Example 10

Isolation of Extracellular Vesicles from Human Urine by Using Calcium Cations (Calcium Chloride)

Human urine was centrifuged at 2,000×g for 15 min (repeated twice in total) to remove remaining precipitates. The supernatant was subjected to addition of calcium cations with several concentrations, followed by mixing and then centrifugation at 3,000×g for 10 min, to thereby harvest precipitates, which were then dissolved in HEPES-buffered saline containing 50 mM EDTA. The extracellular vesicles isolated by the above method were investigated by nanoparticle tracking analysis and western blot analysis.

Figure 11:
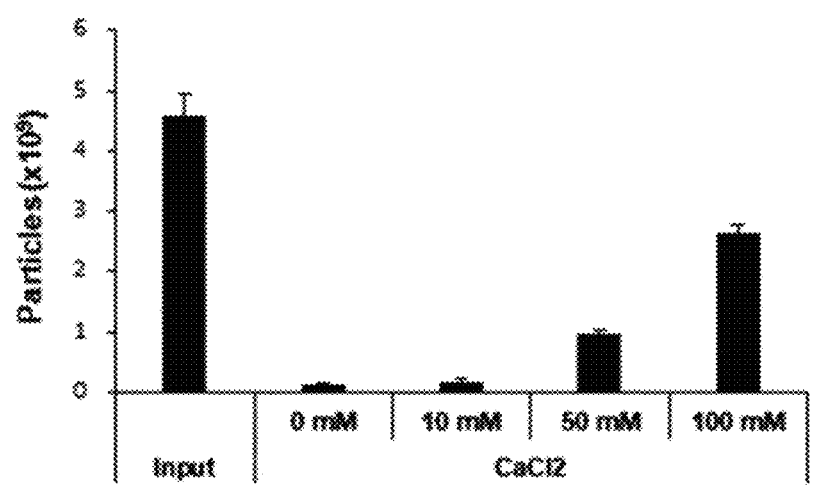
FIG. 11 shows nanoparticle tracking analysis results (FIG. 11A) and western blotting results (FIG. 11B) confirming that extracellular vesicles were isolated from human urine by addition of calcium cations (calcium chloride) with various concentrations according to an example of the present invention.
Figure 11:
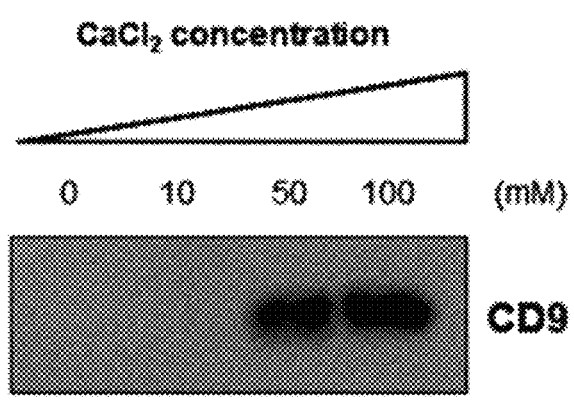

As a result, it was shown in FIG. 11A that the concentration of extracellular vesicles increased as the concentration of calcium cations increased, and it was therefore confirmed in FIG. 11B that the signal of the general extracellular vesicle marker CD9 increased in proportion with the concentration of calcium cations.

Example 11

Isolation of Extracellular Vesicles From Human Urine by Using Manganese Cations (Manganese(II) Sulfate)

Human urine was centrifuged at 2,000×g for 15 min (repeated twice in total) to remove remaining precipitates. The supernatant was subjected to addition of manganese cations with several concentrations, followed by mixing and then centrifugation at 3,000×g for 10 min, to thereby harvest precipitates, which were then dissolved in HEPES-buffered saline containing 50 mM EDTA. The extracellular vesicles isolated by the above method were investigated by nanoparticle tracking analysis and western blot analysis.

Figure 12:
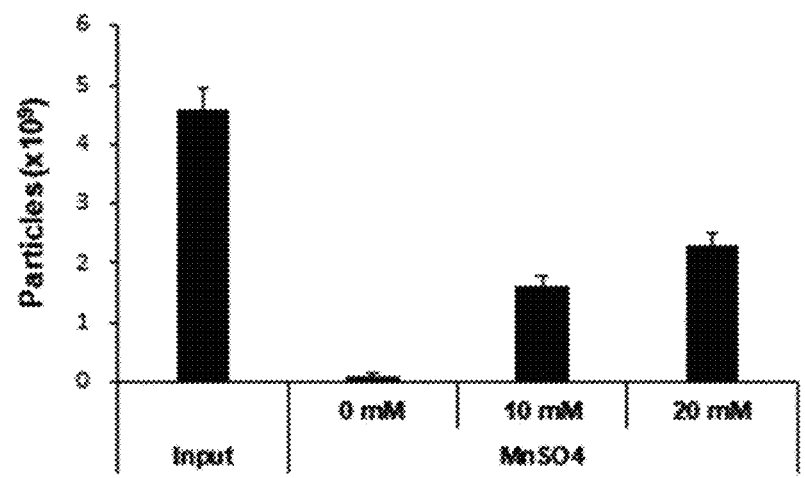
FIG. 12 shows nanoparticle tracking analysis results (FIG. 12A) and western blotting results (FIG. 12B) confirming that extracellular vesicles were isolated from human urine by addition of manganese cations (manganese(II) sulfate) with various concentrations according to an example of the present invention.
Figure 12:
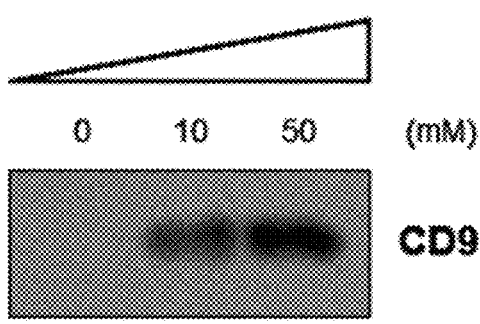

As a result, it was shown in FIG. 12A that the concentration of extracellular vesicles increased as the concentration of manganese cations increased, and it was therefore confirmed in FIG. 12B that the signal of the general extracellular vesicle marker CD9 increased in proportion with the concentration of manganese cations.

Example 12

Isolation of Extracellular Vesicles From Human Urine by Using Zinc Cations (Zinc Chloride)

Human urine was centrifuged at 2,000×g for 15 min (repeated twice in total) to remove remaining precipitates. The supernatant was subjected to addition of zinc cations with several concentrations, followed by mixing and then centrifugation at 3,000×g for 10 min, to thereby harvest precipitates, which were then dissolved in HEPES-buffered saline containing 50 mM EDTA. The extracellular vesicles isolated by the above method were investigated by nanoparticle tracking analysis and western blot analysis.

Figure 13:
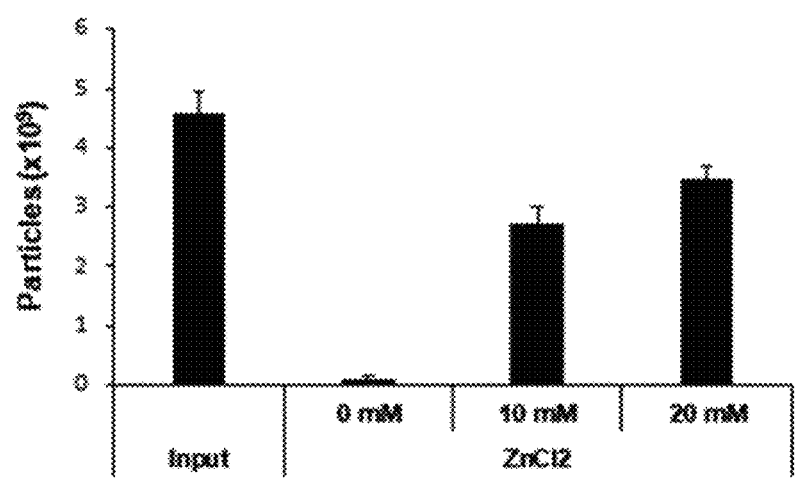
FIG. 13 shows nanoparticle tracking analysis results (FIG. 13A) and western blotting results (FIG. 13B) confirming that extracellular vesicles were isolated from human urine by addition of zinc cations (zinc chloride) with various concentrations according to an example of the present invention.
Figure 13:
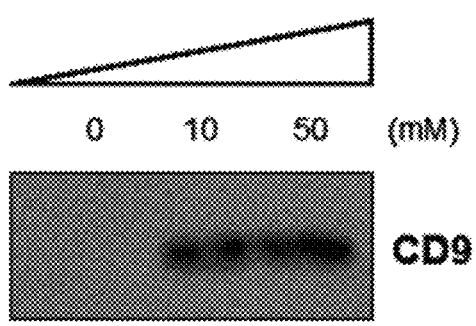

As a result, it was shown in FIG. 13A that the concentration of extracellular vesicles increased as the concentration of zinc cations increased, and it was therefore confirmed in FIG. 13B that the signal of the general extracellular vesicle marker CD9 increased in proportion with the concentration of zinc cations.

Example 13

Increased Isolation Efficiency of Extracellular Vesicles Through Combinations of Various Types of Cations (Copper(II) Chloride and Manganese(II) Sulfate) and Polymers To compare the isolation efficiency of extracellular vesicles according to combinations of various cations and polymers, extracellular vesicles were isolated by addition of cations alone, a polymer alone, or both cations and a polymer.

Specifically, polyethylene glycol (PEG) or poly(2-ethyl-2-oxazoline) (PEOZ) was used as a polymer for isolating extracellular vesicles, wherein only polyethylene glycol (PEG) was added to colorectal cancer cell cultures to reach a final concentration of 8.3%, or only poly(2-ethyl-2-oxazoline) (PEOZ) was added thereto to reach a final concentration of 10%. As for the polymer alone-added groups, extracellular vesicles were harvested through culture at room temperature for 10 min and at 4° C. for 16 hrs and then centrifugation.

As for the cation alone-added groups, only copper cations ($CuCl_2$) or manganese cations ($MnSO_4$) were added to the same cell cultures to reach a final concentration of 20 mM, followed by culture at room temperature for 10 min, and then centrifugation, to thereby harvest extracellular vesicles. Extracellular vesicles were harvested by culture at room temperature for 10 min and then centrifugation also in cases where both the cations and the polymer were added. Thereafter, the precipitated extracellular vesicles were dissolved in the same volume of HEPES-buffered saline.

Figure 14:
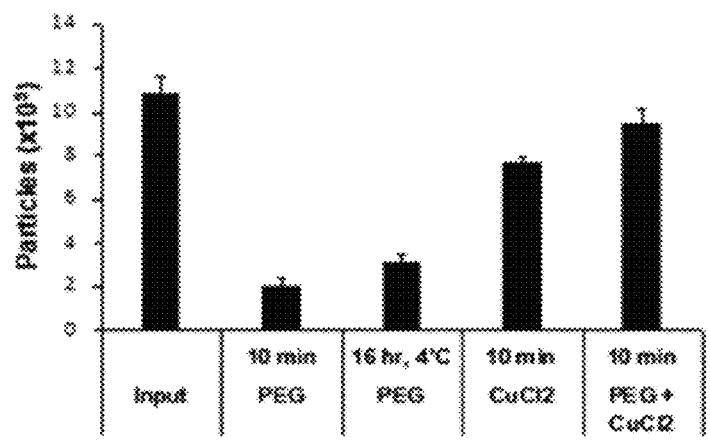
FIGS. 14a, 14b, 14c show nanoparticle tracking analysis results confirming that extracellular vesicles were isolated from cell cultures by the addition of various types of cations (copper(II) chloride and manganese(II) sulfate) and polymers (PEG and PEOZ) together according to an example of the present invention.
Figure 14:
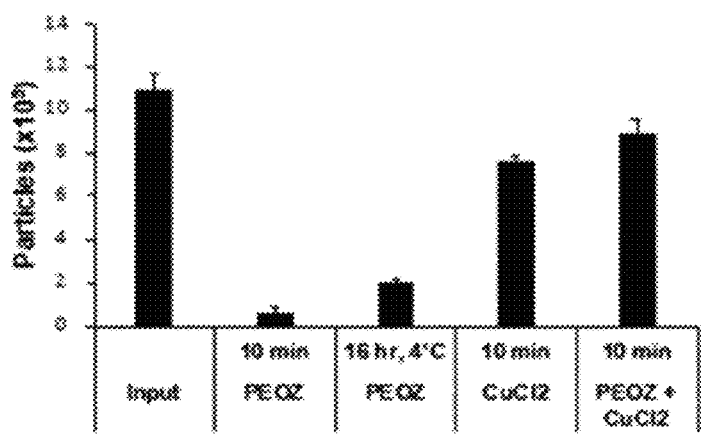
Figure 14:
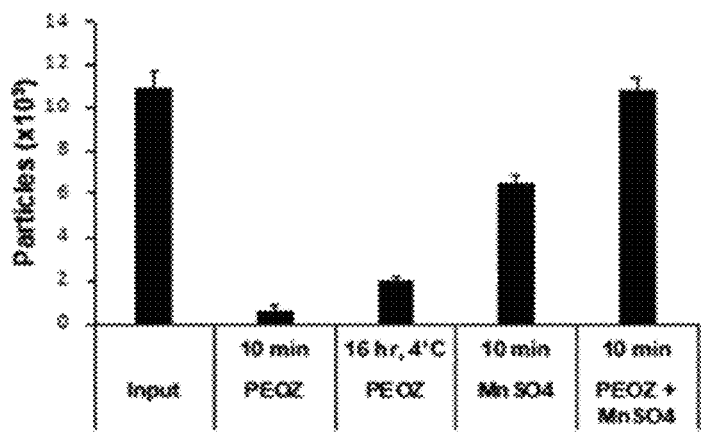

Nanoparticle tracking analysis was performed to compare the yields of extracellular vesicles harvested under the polymer alone, cations alone, or cation-polymer mixed conditions. As shown in FIGS. 14A to 14C, the results verified that the yields of extracellular vesicles under the conditions of culture with cations alone for 10 min were 2-3 times higher than the yields of extracellular vesicles under the conditions of culture for 16 hrs with the polymer alone, and the yields of extracellular vesicles were further increased under the conditions of culture with mixtures of cations and polymers for 10 min. It can be therefore seen that the efficiency is very low for a polymer alone, but the addition of a polymer in the presence of cations further increases the efficiency of the cations to precipitate extracellular vesicles.

Example 14

CD9 Analysis of Extracellular Vesicles According to Concentration of Copper Cations (Copper(II) Sulfate) and Polymer Extracellular vesicles were harvested through centrifugation at 3,000×g for 10 min from: samples obtained by subjecting colorectal cancer cell cultures to addition of copper cations with various concentrations and polyethyl oxazoline to a final concentration of 10% and then culture at room temperature for 30 min; and a sample obtained by culture of the same cell culture with polyethyl oxazoline alone at 4° C. for 18 hrs. To investigate the yields of extracellular vesicles obtained under the respective conditions, the amount of the extracellular vesicle marker CD9 was analyzed through western blotting.

Figure 15:
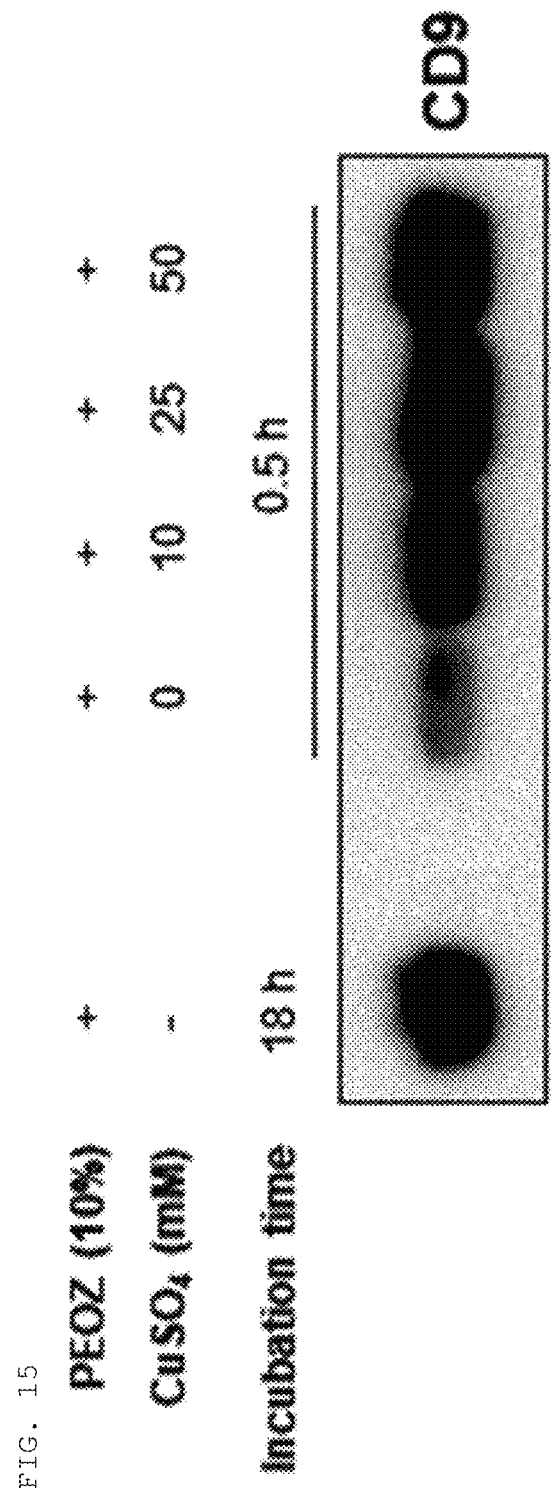
FIG. 15 shows western blotting results confirming that extracellular vesicles were isolated from cell cultures by the addition of copper cations (copper(II) sulfate) and a polymer (PEOZ) together according to an example of the present invention.

As shown in FIG. 15, the results indicated that the yield of extracellular vesicles obtained under the conditions of culture with polyethyl oxazoline alone for 30 min was very low, but in cases of culture for 30 min under the mixed conditions of copper cations with various concentrations and the polymer, the extracellular vesicles were harvested with significantly high yields in proportion with the concentration of copper cations. It can be therefore seen that the efficiency of precipitation of extracellular vesicles is very low for polyethyl oxazoline alone, but the addition of a polymer in the presence of copper cations maximizes the efficiency of precipitation of extracellular vesicles.

Example 15

Isolation of Extracellular Vesicles According to Combination of Ammonium Sulfate and Copper Cations (Copper(II) Sulfate)

Extracellular vesicles were harvested through centrifugation at 3,000×g for 10 min from: samples obtained by adding ammonium sulfate to a final concentration of 1.5 M to a colorectal cancer cell culture, followed by culture at 4° C. for 30 min; samples obtained by adding copper cations (10 mM) alone to the same cell culture; and samples obtained by adding both copper cations and ammonium sulfate to the same cell cultures. Nanoparticle tracking analysis was performed to investigate the yields of extracellular vesicles obtained under the respective conditions.

Figure 16:
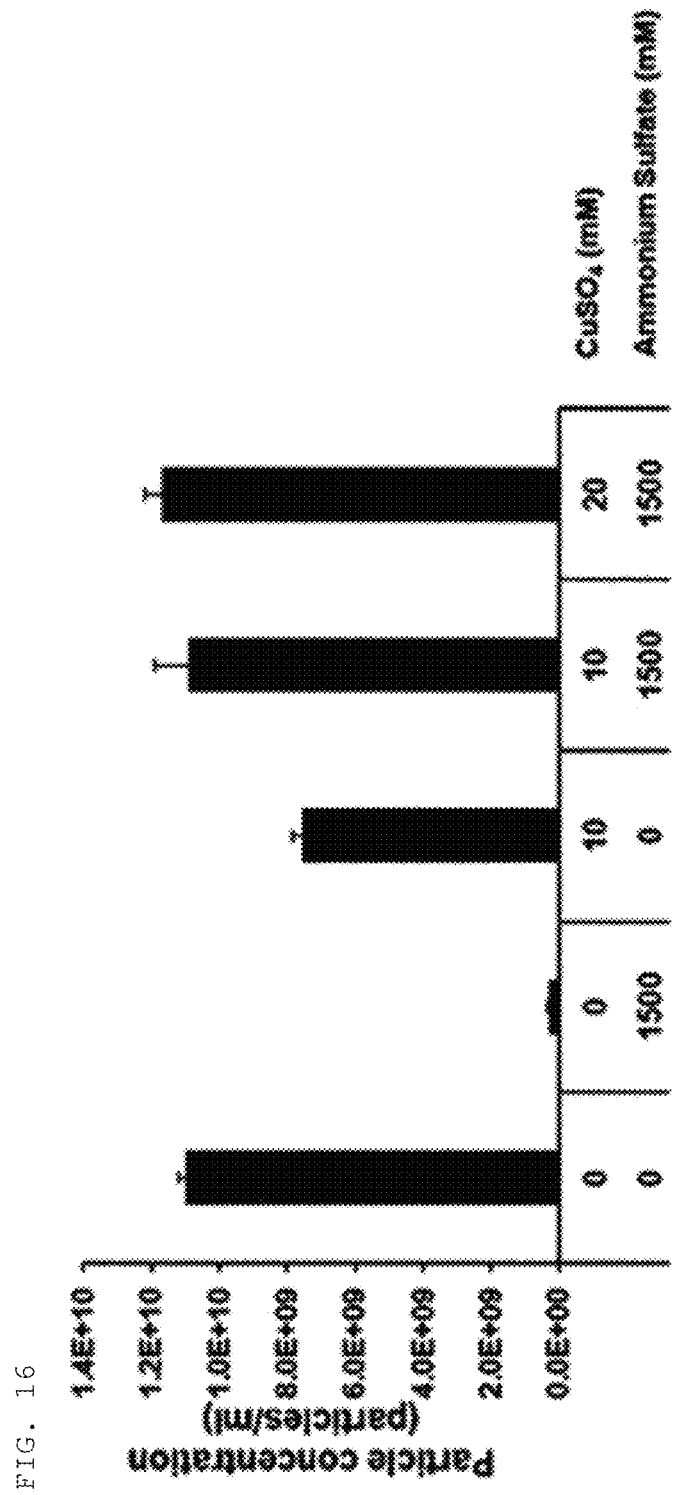
FIG. 16 shows results confirming the isolation of extracellular vesicles by the combination of a conventional salting-out ion (ammonium sulfate) precipitation method and the method of the present invention using copper cations (copper(II) sulfate) according to an example of the present invention.

As shown in FIG. 16, the results indicated that the yield of extracellular vesicles obtained under the conditions of culture with ammonium sulfate alone for 30 min was very low, but a high yield of extracellular vesicles was observed under the conditions of culture with only 10 mM copper cations for 30 min, and the yields of extracellular vesicles present in the samples were further increased in proportion to the concentration of copper cations under the conditions of culture with a mixed of copper cations and ammonium sulfate for 30 min. In cases of short culture for 30 min, the efficiency of precipitation of extracellular vesicles was very low for ammonium sulfate only, but the efficiency of precipitation was excellent for copper cations alone. When the extracellular vesicles were precipitated by addition of both copper cations and ammonium sulfate, the efficiency of copper cations to precipitate extracellular vesicles was maximized.

Example 16

Comparison Between Extracellular Vesicle Isolation Using Polymer and Extracellular Vesicle Isolation Through Copper Cations Following experiment was conducted to analyze differences in yield and purity between extracellular vesicle isolation using a polymer and extracellular vesicle isolation through a polymer-cation combination. For conventional isolation of extracellular vesicles from 10 ml of colorectal cancer cell cultures, polyethylene glycol (PEG) was added to a final concentration of 8.3%, followed by culture at 4° C. for 18 hrs and then centrifugation at 3,000×g for 10 min, and then the precipitates were dissolved in HEPES-buffered saline (20 mM HEPES, pH7.2, 150 mM NaCl). Meanwhile, for the isolation according to the present invention, copper cations were added to the same volume cell cultures, followed by culture for 10 min and then centrifugation at 3,000×g for 10 min, thereby obtaining precipitates, and then the precipitates were dissolved in HEPES buffered saline containing 50 mM EDTA. The samples containing extracellular vesicles isolated by the above method were subjected to additional separation by spin-based size-exclusion chromatography, and then analyzed by size-exclusion chromatography using HPLC system.

Figure 17A:
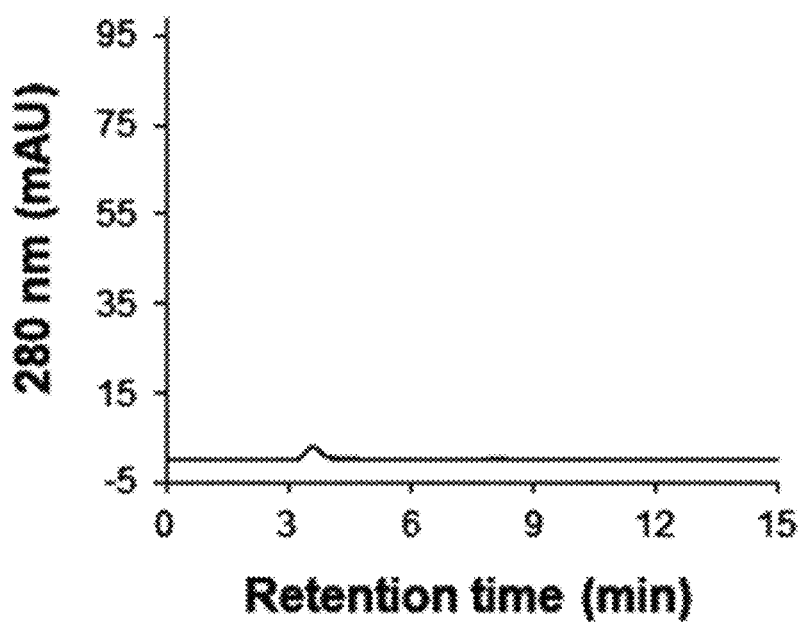
FIG. 17 shows the comparison between the results according to the conventional isolation of extracellular vesicles using polyethylene glycol (PEG) (FIG. 17A) and the results according to the isolation of extracellular vesicles using the method of the present invention (FIG. 17B).
Figure 17B:
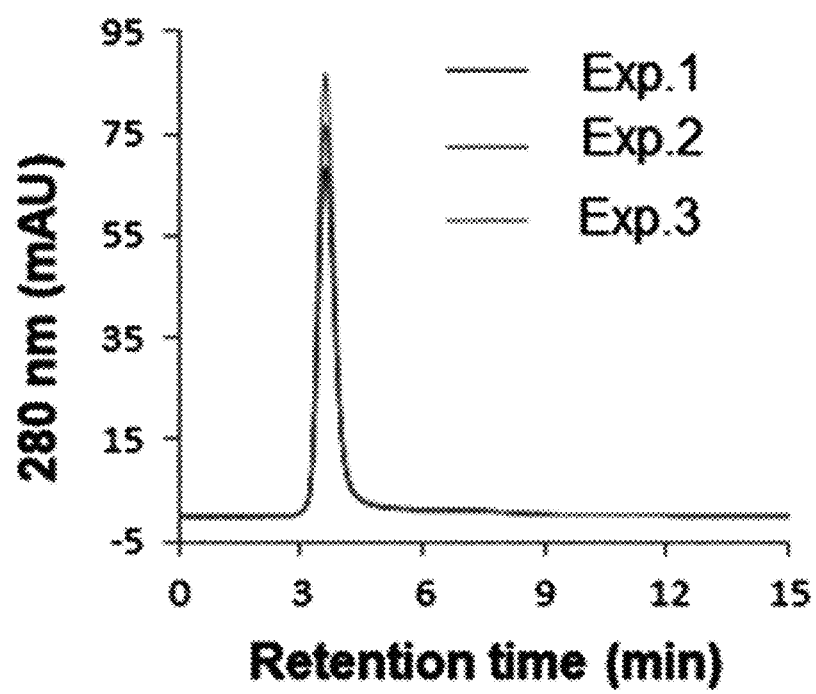

As shown in FIG. 17, the results verified that, compared with a conventional method for isolating extracellular vesicles using a polymer, the use of cations significantly increased the yield and purity of extracellular vesicles.

Although the present invention has been described in detail with reference to the specific features, it will be apparent to those skilled in the art that this description is only for a preferable embodiment and does not limit the scope of the present invention. Thus, the substantial scope of the present invention will be defined by the appended claims and equivalents thereof.

The invention claimed is:

1. A method for isolating extracellular vesicles, the method comprising:
   (a) adding cations to a biological sample containing extracellular vesicles at a concentration sufficient to form an extracellular vesicle-cation insoluble complex, and wherein the cations have a specific affinity for the extracellular vesicles, with the proviso that if the cations are calcium ions, then the calcium ions are added at a concentration of 10 mM or greater, wherein the cations exclude sodium, lithium, or potassium ions;
   (b) inducing a specific binding between the extracellular vesicles and the cations by reacting the cations with the extracellular vesicles contained in the biological sample, thereby forming an extracellular vesicle-cation insoluble complex;
   (c) separating the extracellular vesicle-cation insoluble complex from the biological sample, wherein the separating is performed by using at least one method selected from the group consisting of centrifugation, ultracentrifugation, filtration, ultrafiltration, gravity, density gradient ultracentrifugation, precipitation, polymer-based precipitation, and organic solvent precipitation; and
   (d) separating the cations from the complex to purify the extracellular vesicles.

2. The method of claim 1, wherein the biological sample is at least one sample selected from the group consisting of mammalian cell culture medium, bacterial cell culture medium, yeast culture medium, a tissue extract, a cancer tissue, serum, blood plasma, saliva, tears, sweat, urine, feces, cerebrospinal fluid (CSF), ascites, amniotic fluid, semen, milk, dust, fresh water, seawater, soil, and a fermented food.

3. The method of claim 1, wherein the cations are metal cations.

4. The method of claim 1, wherein step (d) comprises at least one method selected from the group consisting of: adding a chelating agent to the separated extracellular vesicle-cation complex; changing a pH value; and changing the concentration of at least one element selected from the group consisting of imidazole, histidine, ethylenediamine tetraacetate acid (EDTA), and a salt.

5. The method of claim 4, wherein the chelating agent is at least one chemical selected from the group consisting of iminodiacetic acid (IDA), nitrilotriacetic acid (NTA), tris-(carboxymethyl)ethylenediamine (TED), ethylenediamine, ethylenediamine tetraacetate acid (EDTA), alkylene diamine triacetic acid, diethylenetriaminepentaacetic acid (DTPA), ethylene glycol-bis((3-aminoethyl ether)-N,N,N',N'-tetraacetic acid (EGTA), phosphoserine, and 1,4,7-triazocyclononane (TACN).

6. The method of claim 1, further comprising pre-treating the sample before step (a).

7. The method of claim 1, further comprising post-treating the purified extracellular vesicles after step (d).

8. The method of claim 1, further comprising adding a polymer or salting-out ions in step (a).

9. The method of claim 8, wherein the polymer or salting-out ions are added before, simultaneously with, or after the addition of the cations.

10. The method of claim 8, wherein the polymer is polyethylene glycol (PEG) or polyoxazoline.

11. The method of claim 10, wherein the polyoxazoline is poly(2-methyl-2-oxazoline) (PMOZ), poly(2-ethyl-2-oxazoline) (PEOZ), or poly(2-propyl-2-oxazoline) (PPOZ).

* * * * *